(12) United States Patent
Mayr et al.

(10) Patent No.: US 7,494,799 B2
(45) Date of Patent: Feb. 24, 2009

(54) PARAMUNITY INDUCERS BASED ON ATTENUATED RABBIT MYXOMA VIRUS

(75) Inventors: Anton Mayr, Starnberg (DE); Barbara Mayr, Starnberg (DE)

(73) Assignee: Bavarian Nordic A/S, Kvistgaard (DK)

( * ) Notice: Subject to any disclaimer, the term of this patent is extended or adjusted under 35 U.S.C. 154(b) by 3 days.

(21) Appl. No.: 10/587,082

(22) PCT Filed: Jan. 21, 2005

(86) PCT No.: PCT/EP2005/000582

§ 371 (c)(1),
(2), (4) Date: Jul. 21, 2006

(87) PCT Pub. No.: WO2005/070453

PCT Pub. Date: Aug. 4, 2005

(65) Prior Publication Data

US 2007/0154455 A1 Jul. 5, 2007

(30) Foreign Application Priority Data

Jan. 23, 2004 (DE) ............... 10 2004 003 572

(51) Int. Cl.
*C12N 7/04* (2006.01)
*C12N 7/08* (2006.01)
*C12N 7/06* (2006.01)
*C12N 7/01* (2006.01)
*C12Q 1/70* (2006.01)
*C12P 21/04* (2006.01)
*A61K 39/285* (2006.01)
*A61K 39/125* (2006.01)

(52) U.S. Cl. .................. 435/236; 435/5; 435/70.1; 435/235.1; 435/237; 435/238; 424/232.1

(58) Field of Classification Search .................. None
See application file for complete search history.

(56) References Cited

U.S. PATENT DOCUMENTS 6,340,462 B1 * 1/2002 Paoletti .................. 424/199.1
6,805,870 B1 10/2004 Mayr 2003/0013190 A1 * 1/2003 Mayr .................. 435/320.1
2006/0147419 A1 * 7/2006 Perera et al. ............... 424/93.2

FOREIGN PATENT DOCUMENTS

EP 0 669 133 A1 8/1995

OTHER PUBLICATIONS

Ogino et al., Cell Fusion Activities of Hantaan Virus Envelope Glycoproteins, 2004, Journal of Virology, vol. 78, No. 19. pp. 10776-10782.*
Mossman, K. et al., "Myxoma Virus M-T7 a Secreted Homolog of the Interferon-γ Receptor, Is a Critical Virulence I-Actor for the Development of Myxomatosis in European Rabbits," Virology, vol. 215, Article No. 0003, pp. 17-30, (1996).
Upton, C. et al., "Myxoma Virus Expresses a Secreted Protein with Homology to the Tumor Necrosis Factor Receptor Gene Family that Contributes to Viral Virulence," Virology, vol. 184, pp. 370-382, (1991).
Saito, J. K. et al., "Attenuation of the Myxoma Virus and Use of The Living Attenuated Virus as an Immunizing Agent for Myxomatosis," The Journal of Infectious Diseases, vol. 114, pp. 417-428, (Dec. 1964).
McCabe, V. J. et al., "Vaccination of Cats with an Attenuated Recombinant Myxoma Virus Expressing Feline Calicivirus Capsid Protein," Vaccine, vol. 20, pp. 2454-2462, (2002).
Nash, P. et al., "Immunomodulation by Viruses: The Myxoma Virus Story," Immunological Reviews, vol. 168, pp. 103-120, (1999).
Mayr, A. et al., "A New Concept in Prophylaxis and Therapy: Paramunization by Poxvirus Inducers," Pesq. Vet. Bras., vol. 19, No. 3/4, pp. 91-98, (Jul. 1999).
Büttner, M., "Principles of Paramunization: Option and Limits in Veterinary Medicine," Comp. Immun. Microbiol. Infect. Dis., vol. 16, No. 1, pp. 1-10, (1993).

* cited by examiner

*Primary Examiner*—Bruce Campell
*Assistant Examiner*—Benjamin P Blumel
(74) *Attorney, Agent, or Firm*—Law Office of Salvatore Arrigo

(57) ABSTRACT

The invention relates to monoparamunity inducers that are based on paramunizing viruses or viral components of a myxoma virus strain of diseased rabbits that show general symptoms of the disease. The invention also relates to a method for producing the inducers and to their use as drugs for the regulatory optimization of the paramunizing activities for use in the prophylaxis and therapy of various human and animal dysfunctions.

21 Claims, No Drawings

PARAMUNITY INDUCERS BASED ON ATTENUATED RABBIT MYXOMA VIRUS

This application is a National Stage Application of International Application No. PCT/EP2005/000582, filed Jan. 21, 2005, which claims the benefit of German Patent Application No. DE 10 2004 003 572.5, filed Jan. 23, 2004.

The invention relates to monoparamunity inducers based on paramunizing viruses or viral components, characterized in that the viruses or viral components are derived from an attenuated rabbit myxomavirus strain, to a method for producing the monoparamunity inducers and to the use thereof as medicaments.

The endogenous immune system of highly developed organisms, especially that of mammals and birds, includes an antigen-specific and an antigen-nonspecific part. Both parts of the immune system are linked together and moreover interact with one another. The antigen-specific mechanisms are responsible for building up immunity, and the antigen-nonspecific are responsible for building up paramunity. Paramunity refers to the state of a well regulated and optimally functioning nonspecific defense system linked to a rapidly developing, time-limited, increased protection from a large number of different pathogens, antigens and other noxae. The basis for the development of paramunity are, for historical and functional reasons, the nonselective and conditionally selective paraspecific defense mechanisms which are old from the phylogenetic viewpoint and are called primitive.

The paraspecific activities of the antigen-nonspecific immune system (also: "innate immune system") include nonselective protective elements such as, for example, foreign material-consuming organelles, and conditionally selective protective elements such as, for example, micro— and macrophages, natural killer cells, dendritic cells and soluble factors such as cytokines, which show pathogen-nonspecific or antigen-nonspecific reactions according to their origin.

Paraspecific activities are to be observed in the relevant organism immediately after antigen contact, whereas the effects of the antigen-specific immune system appear only after days or weeks.

In the more highly organized life forms, time is additionally gained thereby in order to build up specific defense systems against the noxae which it has not yet been possible to eliminate and have antigenic properties.

The benefits of paramunization i.e. the paraspecific activities of the immune system for prophylaxis and therapy in a patient have become increasingly clear since its development (Anton Mayr, "Paramunisierung: Empirie oder Wissenschaft", Biol. Med. edition 26(6): 256-261, 1997). The paraspecific defenses make it possible for the organism to defend itself immediately on confrontation with a wide variety of foreign materials, infectious pathogens, toxins and transformed endogenous cells.

There are close interactions between the paraspecific and the specific activities of the immune system, with the flow of information usually proceeding from the initially reacting paraspecific part to the specific part, with a later onset, of the immune system (e.g. with antigen mediation). In the event of infections with particularly virulent pathogens, the paraspecific defenses of the organism are able in this way to cover the time until specific immunity develops (e.g. antibodies, immune cells).

The paraspecific immune defenses are a physiological process and can be defined as "primary control" in the confrontation with the environment. They are indispensable not only for lower organisms but in particular also for the more highly developed and highly developed vertebrates. Primary congenital defects in this biological defense system lead to life-threatening situations. An example which may be mentioned is the "Chediak-Steinbrinck-Higashi syndrome" in humans, which is characterized by granulocyte deficits and dysfunctions of natural killer cells (NK cells) and in most cases leads to the death of the patient by completion of the 10th year of life.

The condition of paramunity is characterized by an increased rate of phagocytosis, an increased function of the spontaneous cell-mediated cytotoxicity (NK cells) and increased activity of other lymphoreticular cells. At the same time there is release of particular cytokines which have stimulating and/or inhibiting effects (e.g. via repressor mechanisms) both with the cellular elements and with one another. This closely linked and stepwise responding biological system of paramunity with its various acceptor, effector and target cells and the signal-transmitting cytokines is moreover thoroughly connected to the hormonal and nervous systems. It thus represents an important constituent of the communication, interaction and regulation network.

Paramunity is induced by paramunization. By this is meant the pharmacological activation of the cellular elements of the paraspecific part of the immune system and the production, associated therewith, of cytokines, with the aim of eliminating dysfunctions, rapidly increasing the non-pathogen- and non-antigen-specific protection of an individual (optimal bioregulation), eliminating an immunosuppression or immunodeficiency which has arisen from the consequences of stress or otherwise (e.g. pharmacologically), repairing deficits and/ or acting as regulator between the immune, hormonal and nervous systems. This means that certain nonspecific endogenous defense processes can be increased, supplemented or else depressed, depending on the type of paramunization and the responsiveness, such as, for example, the health status of the patient.

Paramunity inducers are used for the paramunization and must meet certain criteria of harmlessness and efficacy, thus differing from immunostimulants. The paramunity inducer per se is not comparable either to an antibody or to a chemical, an antibiotic, vitamin or hormone. On the contrary, it activates by a stepwise mechanism the paraspecific immune system, so that the latter sufficiently mobilizes cellular and humoral defense mechanisms. The paramunity inducer in this case has both regulating and repairing effects on the immune defenses. Concerning the mode of action of paramunity inducers, it is known that they are taken up by phagocytic cells (acceptor cells) which are thus activated and release mediators which in turn mobilize effector cells. The latter finally switch on the regulatory mechanisms of the paraspecific defenses.

Multiple paramunity inducers based on combinations of two more poxvirus components derived from different poxvirus strains with paramunizing properties are described in European patent EP 0 669 133 B1.

The present invention is based on the paramunizing properties of attenuated myxomaviruses and/or their viral constituents.

Attenuation refers to the modification of the properties of an infectious pathogen which lead to weakening of the pathogen ("attenuate"=weaken, mitigate). Alterations in infectious pathogens frequently occur spontaneously in nature, it being possible for the timespans to extend over many centuries.

The ability of infectious pathogens to change in order to adapt to environmental changes can be utilized experimentally, and the timespan necessary for attenuation can be drastically shortened for example by long-term passages in certain host systems. Attenuation has been utilized to date to obtain avirulent inoculation strains and harmless paramunity inducers.

Attenuation normally leads to loss of virulence and contagiousness, reduction in the immunizing properties and the host range, and to small changes in the pathogen genome with the occurrence of deletions, preferably in the terminal regions. There is usually parallel increase in the paramunizing activities of the modified pathogen.

In rare cases, an attenuation may, especially when an experimental attenuation by genetic manipulations is attempted, also lead to an increase in the virulence and contagiousness.

Myxomaviruses are the pathogens of myxomatosis, a contagious systemic viral disease of wild and domestic rabbits which progresses in cycles and is characterized by generalized, in some cases hemorrhagic subcutaneous edemas on the head and over the entire body, with preference for the anal region, the vulva and the tube, unlike any other infectious disease. Introduction of myxomatosis into a country previously free of the disease results in rapid and fatal progression. After the virus has become endemic, the character of the disease changes until the infections are clinically inapparent (Mayr A.: Medizinische Mikrobiologie, Infections—und Seuchenlehre, 7th edition, Enke-verlag, Stuttgart, 2002).

The disease is widespread among American cottontail rabbits of the genus *Sylvilagus* which occupy exclusively the New World. These wild rabbits form the only natural reservoir of the disease. The infection takes a mild form in them. By contrast, the disease has an almost 100% mortality in European wild and domestic rabbits of the genus *Oryctolagus*, which are also naturalized in Australia, when the pathogen is introduced.

The natural host range of the myxomavirus (genus *Leporipoxvirus*) has narrow limits. In general, the virus replicates only in American cottontail rabbits and in European domestic and wild rabbits. However, a few infections in European wild hares have also been observed. Attempts at transmission to other species and to humans had negative results.

The present invention is based on the object of providing novel monoparamunity inducers for human medicine and veterinary medicine. A further object of the present invention is to provide a method for producing such monoparamunity inducers. It is additionally an object of the present invention to provide pharmaceutical compositions for use as medicaments based on monoparamunity inducers.

Accordingly, the present invention relates to monoparamunity inducers based on paramunizing viruses or viral components, characterized in that the viruses or viral components are derived from an attenuated rabbit myxomavirus strain. The viral components preferably include paramunizing viral envelopes or aberrant forms of viral envelopes of an attenuated myxomavirus strain. Preferred strains having the paramunizing properties of the invention are the strains M-2, M-7, Lausanne, Aust/Uriarra/Verg-86/1. The strains M-7, Lausanne, Aust/Uriarra/Verg-86/1 are also suitable for producing live vaccines because they have undergone only partial attenuation of their virulence in order to have an adequate immunizing effect.

A monoparamunity inducer based on the myxomavirus strain M-2 is particularly preferred. An attenuated myxomavirus strain produced by the method of the invention described hereinafter has been deposited at the depository of the Public Health Laboratory Service (PHLS), Centre for Applied Microbiology & Research, European Collection of Animals Cell Cultures (ECACC), Salisbury, Wiltshire, United Kingdom with the deposit number 03121801.

The invention further relates to a method for producing monoparamunity inducers based on an attenuated rabbit myxomavirus strain. For this purpose, initially myxomaviruses are isolated from infected tissue of a rabbit typically suffering from a generalized myxomatosis. The virus is subsequently adapted to a permissive cell system, i.e. to a cell material which permits replication of the virus, such as, for example, cell cultures, incubated chicken eggs or else experimental animals. It is possible in particular to use cells of the natural host or of a species closely related to the host for the adaptation. Examples of suitable permissive cell systems for myxomaviruses are chick embryo fibroblasts (CEF) as well as cell cultures produced from rabbit kidneys or testes.

It is preferred according to the invention to adapt the isolated myxomavirus to the chorioallantoic membrane (CAM) of incubated chicken eggs over one or more passages, preferably over 2 to 6 passages, and particularly preferably over 3 passages. For this adaptation, the isolated viruses are inoculated onto the CAM and replicated by passaging on the CAM.

The myxomaviruses are preferably initially isolated from infected tissue by replication in a permissive cell system. For this purpose it is possible to inoculate a permissive cell system for example with infected tissue homogenate obtained by disruption. Subsequently, the viruses obtained by the initial replication are either adapted further to the same permissive cell system, which was already used for the isolation, or another, further permissive cell system is used. Adaptation of the virus to the same permissive cell system type which is also used for the isolation is preferred. Thus, preferably myxomaviruses from infected tissue are isolated by replication in a permissive cell system and subsequently adapted to the permissive cell system by further passages. Initial culturing and isolation of the myxomaviruses by replication on the CAM of incubated chicken eggs and subsequent adaptation of the virus on the CAM over further passages, preferably over a further 2 passages, is particularly preferred. However, it is also possible alternatively to use the allanotoic fluid of incubated chicken eggs for the culturing and/or adaptation.

The actual attenuation then takes place by long-term passages on one or more permissive cell cultures, until an attenuation or the desired degree of attenuation of the virus is reached. It is possible for this purpose firstly to test various permissive cell systems for replication of the virus and subsequently to select one or more cell systems in which the highest infectious titers are reached for further passages. Both primary and secondary cell cultures as well as permanent and continuous cell lines are suitable for attenuation by long-term passages. Thus, attenuation can take place by replication in primary or secondary chick embryo fibroblast (CEF) cultures or in cultures of permanent CEF cells.

Preferred according to the invention for attenuation of the myxomavirus is to passage or replicate the virus in a permanent cell culture, in particular a Vero cell culture, preferably over 80 to 150 passages and particularly preferably over 120 passages. Alternatively or additionally, the virus is passaged according to the invention on a binary permanent cell line, in which case AVIVER cells are preferably used. These cells or cell culture has been obtained by cell fusion between chick embryo fibroblasts (CEF) and Vero monkey kidney cells. For the myxomavirus attenuation of the invention, the isolated and adapted viruses are preferably passaged in a first step in Vero cell cultures, the viruses are then transferred into a binary AVIVER cell culture and replicated therein preferably over 10 to 50 passages, in particular over 20 to 30 passages, and particularly preferably over 25 passages.

The attenuated myxomavirus can then be additionally replicated over further attenuation passages. Further replication of the viruses preferably takes place over further passages in Vero monkey kidney cells, in particular over 100 to 200 passages.

A particularly preferred further method step is additional inactivation of the attenuated myxomavirus. Inactivation can take place by chemical treatment, irradiation, the action of heat or pH, in particular by a chemical treatment with beta-propiolactone. Treatment of the attenuated myxomaviruses with beta-propiolactone increases the paraspecific activities further, while the immunizing properties which are still present where appropriate after the attenuation are lost.

A particularly preferred embodiment of the method of the invention includes the following steps:
- isolation of myxomaviruses from the infected tissue of a rabbit suffering typically from generalized myxomatosis by replication on the chorioallantoic membrane (CAM) of incubated chicken eggs and subsequent adaptation of the virus to the CAM over a further 2 passages;
- attenuation of the isolated viruses by passaging in Vero cell cultures, preferably over 120 passages;
- transfer of the viruses into a binary AVIVER cell culture, where the AVIVER cells have been obtained by cell fusion between chick embryo fibroblasts (CEF) and Vero monkey kidney cells, and attenuation of the virus in this cell culture over 10 to 50, preferably 25, passages,
- subsequent transfer of the virus back onto Vero monkey kidney cells and replication of the viruses by further attenuation passages in the Vero cells, preferably over about 150 passages; and optionally
- inactivation of the attenuated myxomaviruses by treatment with beta-propiolactone, this treatment increasing the paraspecific activities, while the immunizing properties still present after the attenuation are lost.

Attenuation by long-term passaging is usually concluded by 3 to 5 plaque end dilutions. After various clones have been obtained and tested, the clones selected for further replication are those with which the highest infectious titers are achieved and with which a high paramunizing activity—e.g. in the VSV challenge test in the baby mouse—are detected. This procedure is intended to ensure in particular that genetically uniform virus material is provided for further use.

The term "attenuation" as used in connection with this invention refers to the experimental modification of the originally virulent myxomavirus into the modified form, with a simultaneous increase in the paramunizing properties. The attenuation is detectable through one or more of the following properties:
- reduction or weakening or loss of virulence for European domestic and wild rabbits (genus *Oryctolagus caniculus* csp.),
- weakening or loss of contagiousness,
- restriction of the host range in cell cultures,
- alteration of the immunizing properties
- acquisition of paramunizing, short-term protective activities.

An attenuation may lead to deletions in the terminal region of the myxomavirus genome. An increasing degree of attenuation is frequently observed to be associated with an increasing number of deletions in the viral genome.

The degree of attenuation can be checked and monitored during the passages by appropriate suitable activity tests as known in the art (cf., for example, U.S. Pat. No. 6,805,870, column 12, and the further references cited therein) and by cloning.

The present invention further relates to attenuated myxomaviruses obtainable by the method of the invention, pharmaceutical compositions including the attenuated myxomavirus or the myxomavirus mono-paramunity inducer of the invention, and to the use of the myxomavirus monoparamunity inducers for activating the paraspecific immune system in a mammal and to the use of the attenuated virus for producing a corresponding medicament.

Because of the surprising paramunizing properties, the myxomavirus monoparamunity inducers of the invention are suitable for the treatment and/or for the prophylaxis of immune system dysfunctions, immuno-suppression, immunodeficiency disorders, dysfunctions of homeostasis between the hormonal, circulatory, metabolic and nervous systems, threatened neonatal infection, neoplastic diseases, viral diseases, bacterial diseases, therapy-resistant infectious factor diseases, viral and bacterial mixed infections, chronic manifestations of infectious processes, liver disorders of various etiologies, chronic skin disorders, herpetic diseases, chronic hepatitides, influenzal infections, endotoxin damage.

The monoparamunity inducers of the invention are generally harmless to the environment and effective in the sense of paramunization for mammals such as, for example, humans, horses, dogs, cats, pigs, for birds and also for reptiles such as, for example, lizards, snakes, chelonians. They are therefore particularly suitable for use in human and veterinary medicine.

In addition, the monoparamunity inducers of the invention display a very good paramunizing activity with high potency. They can be produced by the method of the invention in a suitable manner and are safe for use in the medical sector. The attenuation of the myxomaviruses reduces the immunizing properties of the myxomaviruses while the paraspecific activities increase. The monoparamunity inducers of the invention therefore have paramunizing, but no immunizing, properties, making multiple and continuous use possible. These paramunizing properties of the rabbit myxomavirus and of its paramunizing viral components are surprising and were not predictable.

The term "paramunization" as used in connection with this invention refers to the pharmacological activation of the cellular elements of the paraspecific immune system and the production or release, associated therewith, of cytokines with the aim of eliminating dysfunctions, rapidly increasing the non-pathogen- and non-antigen-specific protection of an individual, and having a regulatory effect between the immune, hormonal, nervous and vascular systems. Paramunization leads to the protected state of paramunity.

The term "paramunity" as used in connection with this invention refers to the actively acquired state of an optimally regulated and functioning paraspecific defense system, associated with a rapidly developing, time-limited protection from a large number of pathogens, antigens and other noxae. The phagocytosis rate, the function of the NK cells (natural killer cells) and the activity of other lymphoreticular cells (e.g. dendritic cells) are raised to the physiological optimum.

The term "paramunity inducer" as used in connection with this invention refers to a pyrogen-free, nontoxic medicament which is intended to be used in humans and animals to generate and regulate endogenous defense and protective mechanisms in the sense of paramunization.

The term "myxomavirus monoparamunity inducer" as used in connection with this invention refers to a medicament which is based on attenuated rabbit myxomaviruses or an attenuated myxomavirus strain, including the paramunizing viral components and the constituents thereof which produce the state of paramunity in an organism, preferably in a mammal (e.g. human).

The term "myxomavirus" as used in connection with this invention refers to the species of the myxomatosis virus of the genus *Leporipoxvirus*. The myxomavirus belongs to the subfamily of Chordopoxviridae and to the family of Poxviridae (poxviruses).

The term "paramunizing viral components" as used in connection with this invention includes a large number of viral structures derived from a myxomavirus having paramunizing properties, for example viable or inactivated freshly isolated myxomaviruses, viable or inactivated recombinant myxomaviruses derived from freshly isolated myxomaviruses, viral envelopes, the removed envelopes and cleavage products and aberrant forms of these envelopes, individual native or recombinant polypeptides or proteins, in particular membrane and surface receptors which occur in freshly isolated myxomaviruses or are recombinantly expressed by a genetically modified myxomavirus or a part of its genetic information.

Tables 1 to 4 summarize the clinical results with the myxomavirus monoparamunity inducer PIND-MYXO based on the attenuated myxomatosis cell culture virus, strain M-2, in humans.

Table 1 shows the clinical results on prophylactic use of the myxomavirus monoparamunity inducer PIND-MYXO in humans.

Table 2 shows the clinical results on therapeutic use of the myxomavirus monoparamunity inducer PIND-MYXO in humans.

Table 3 shows the effect of paramunization with myxomavirus monoparamunity inducer (PIND-MYXO) in patients with low immune parameters (7 days after PIND-MYXO administration).

Table 4 shows the effect of paramunization with myxomavirus monoparamunity inducer (PIND-MYXO) in patients with elevated immune parameters (7 days after PIND-MYXO administration).

The invention is based on the surprising finding that attenuated rabbit myxomaviruses or their paramunizing constituents are able to induce very good paramunizing properties in a recipient organism which lead to the protected state of paramunity. The basis for this invention was the first successful attenuation of rabbit myxomaviruses in cell cultures.

The monoparamunity inducers of the invention are preferably based on lyophilized, attenuated and inactivated rabbit myxomaviruses or their paramunizing viral components. The attenuated myxomaviruses or their viral components of the invention are preferably derived from one myxomavirus strain or a plurality of different attenuated myxomavirus strains. It is preferred in this connection for the monoparamunity inducers of the invention to include combinations of one or more myxomavirus strains or their paramunizing viral components.

The paramunizing properties induced in a mammal such as, for example, in humans through administration of myxomavirus monoparamunity inducer are particularly beneficial for eliminating dysfunctions, for increasing the non-antigen-specific protection of an individual, for eliminating an immunosuppression or immuno-deficiency which has arisen from the consequences of stress or in other ways (e.g. pharmacological) and in order to have regulatory effects between the immune, hormonal and vascular systems.

The invention is further based on successful attenuation of a myxomavirus strain by passaging through cell cultures, with the virulent and/or immunizing properties of the myxomavirus strain being reduced or lost. Additional inactivation of the myxomaviruses can moreover take place by irradiation, the action of heat or pH, or, particularly preferably, by a chemical treatment with beta-propiolactone. The monoparamunity inducers are based on attenuated, lyophilized myxomaviruses, with individual viral components of a myxomavirus which are suitable for inducing paramunizing activities in an organism also being encompassed by the invention.

It is intended below to describe one embodiment of the production method of the invention for monoparamunity inducers based on an isolated and attenuated rabbit myxomavirus strain via cell culture passaging. The production method is moreover not restricted to this preferred strain, but can be applied in the same way to other rabbit myxomavirus strains. Also encompassed by the present invention are recombinant forms of a myxomavirus strain which have been produced by genetic modification. Preference is given in this connection to recombinant myxomavirus strains in which one or more segments in the genome which code for cytokine receptors has been modified by a modification in the form of an addition, substitution or deletion, with the receptor properties of the cytokine receptor being lost through the modification. These are preferably the gene segments which code for the receptors for interferons (IFN), interleukins (IL) and tumor necrosis factors (TFN), in particular for IFN-$\alpha$-R, IFN$\gamma$-R, TNF-R, IL-1-R, IL-2-R, IL-6-R and IL-12-R.

In addition, the numerical values stated herein concerning the incubation time or the number of passages over cell cultures are not intended to be regarded as restrictive. Slight modifications of these parameters and modifications evident to the skilled worker and also leading to a preparation of attenuated myxomaviruses are equally encompassed by this invention.

A preferred embodiment of the present invention relates to the successful attenuation of the myxomavirus strain M-2. The myxomavirus strain M-2 was isolated from European wild rabbits suffering from myxomatosis (Herrlich A., Mayr A. and Munz E.: "Die Pocken", 2nd edition, Georg Thieme Verlag, Stuttgart, 1967). The altered skin cells obtained from the subcutaneous tissue of the diseased rabbit are, after disruption, inoculated onto the chorioallantoic membrane (CAM) of chicken eggs which have been incubated preferably for 10-12 days. The myxomaviruses are further replicated and adapted over 2 to 6 passages, preferably over 3 passages, on the chorioallantoic membrane (CAM passages; for method, see Herrlich A., Mayr A. and Munz E.: "Die Pocken", 2nd edition, Georg Thieme Verlag, Stuttgart, 1967). The 2nd to 6th passage, preferably the third CAM passage, serves as starting material for the further attenuation of the myxomavirus in cell cultures. The attenuation takes place after adaptation of the viruses in the chorioallantoic membrane (evident from typical foci on the chorioallantoic membrane) in 3 stages. In stage 1, to 150, preferably 120, continuous so-called end-dilution passages take place in Vero cells (Vero cells, ATCC CCL-81). The virulence of the myxomavirus which has undergone these passages is weakened.

In a 2nd stage after the 80th to 150th passage, preferably after the 120th passage, in Vero cells, the viral suspension is transferred to so-called AVIVER cells and continued over 10 to 50 passages, preferably over 20 to 30, in particular over 25, passages. AVIVER cells are obtained by cell fusion between chick embryo fibroblasts (CEF) and Vero cells and are referred to as binary permanent cell culture.

The last passage over AVIVER cells, preferably the 25th passage, is transferred back to Vero cells and is continued in the 3rd stage of attenuation for a further 100 to 200 passages, preferably about 157 passages, in Vero cells. In this way, the myxomavirus is replicated over a total of more than 300 cell culture passages. After the 3rd stage of replication of the myxomavirus in cell cultures, the myxomavirus is sufficiently attenuated.

The Vero cell cultures and the AVIVER cells are preferably cultured using a completely synthetic medium, particularly preferably the MEM medium (minimal essential medium) plus 5 to 20%, preferably 10%, BMS (serum substitute medium) and 5 to 20, preferably 10%, lactalalmin hydrolysate. The virus medium used after exchange with the culture medium is preferably MEM medium with 5 to 20%, preferably with 10%, lactalalbumin hydrolysate, without BMS or without fetal calf serum and without antibiotics. All the production methods are preferably carried out at pH values of 7.0 to 8.0, preferably at a pH of 7.25. Virus harvests with titer from $10^{5.0}$ to $10^{7.5}$, preferably of at least $10^{6.5}$ TCID$_{50}$/ml (TCID$_{50}$=50% tissue culture infectious dose) are preferably suitable as starting material for producing the monoparamunity inducer PIND-MYXO of the invention.

Replication of the myxomavirus in Vero cells leads to a typical cytopathic effect (cpE) which is ultimately characterized by a destruction of the infected cells (lysis). Inoculation with a dose of about 10 MOI (multiplicity of infection) results after a short rounding phase (1-2 days) in reticulated cell structures for about 3 days and in lysis of the cells after about 5 days. The 301st passage in Vero cells had an infectious titer of about $10^{6.5}$ TCID$_{50}$/ml.

The attenuated myxomavirus is inactivated by a chemical treatment with beta-propiolactone at a concentration of 0.01-1% beta-propiolactone, preferably at a concentration of 0.05% beta-propiolactone. This inactivation leads to a complete loss of the immunizing properties which are still present where appropriate, while the paraspecific activities are not only retained but in fact significantly increase.

For further processing of the attenuated and inactivated myxomaviruses to a myxomavirus monoparamunity inducer (PIND-MYXO), the virus starting material used for the virus inactivation should have a viral titer of about $10^{5.0}$ to $10^{7.0}$, preferably of at least $10^{6.5}$, TCID$_{50}$/ml.

Purification preferably takes place by centrifugation at low revolutions (e.g. 1000 rpm). After the centrifugation, 0.5-10% succinylated gelatin (e.g. polygeline, e.g. from Hausmann, St Gallen/Switzerland), preferably 5% succinylated gelatin, is added. The resulting mixture can subsequently be lyophilized in 1.5 ml portions in appropriate sterile glass vials or ampoules and, if required, dissolved in distilled water. A volume of 0.5-2 ml, preferably of 1.0 ml of the lyophilisate dissolved in distilled water corresponds to an inoculation dose for humans on intramuscular administration (see also Mayr A. and Mayr B.: "Von der Empirie zur Wissenschaft", Tierärztl. Umschau, edition 56: 583-587, 2002).

The attenuation can be detected clinically through the loss of virulence for European domestic and wild rabbits (genus *Oryctolagus caniculus* csp.), through a loss of contagiousness, through a virtually complete restriction of the host range in cell cultures and through the alteration in the immunizing properties.

The lyophilized product can be stored at temperatures of, preferably, about +4° C. or at lower temperatures, preferably about −60° C., with stability for an unlimited time.

It was demonstrated by gene technology investigations of the prepared attenuated myxomaviruses that multiple deletions had occurred in the myxomavirus genome. In the case of the initial strain M-2, the myxomavirus genome consists of a single linear deoxyribonucleic acid (DNA) with a total length of about 160 kilobases (kb), which codes for several hundred proteins (Herrlich A., Mayr A. and Munz E.: "Die Pocken", 2nd edition, Georg Thieme Verlag, Stuttgart, 1967). The sequences of the terminally located inverted repeats (terminal inverted repeats, TIR) are situated at about 11 kb of the genome segment (McFadden, G. and Graham K.: "Modulation of cytokine networks by pox virus", Virology, edition 5: 421-429, 1994).

Thus, it has been found that the attenuation of the myxomaviruses over continuous Vero cell passages has led to a loss of the coding gene segments for the receptors for interferon α and γ (IFN α, IFNγ), for tumor necrosis factor (TNF) and for the interleukins (IL) 1, 2, 6 and 12. It is of interest that these cytokines belong to the paraspecific defense factors of the nonspecific immune system. The cytokines are neutralized by binding to the corresponding viral receptors, so that the virus is able to replicate unimpeded. The deletions of gene segments which code for the abovementioned cytokine receptors relate mainly to the terminal regions of the DNA. However, it was additionally possible to detect deletions which occured during the AVIVER cell passages in the conserved part of the DNA. These deletions relate to two genes which code for an immune epitope and virulence gene. Such genetic modifications are presumably one of the reasons for the decrease in the immunizing, i.e. antigen-specific, activities and the simultaneous increase in the paraspecific activities of the attenuated myxomavirus.

The immunizing epitopes and the paraspecific and nonspecific epitopes are in competition. A decrease in the first-mentioned peptides or proteins therefore leads to an increase in the effect of the paraspecific activities. Residues of immunizing and virulence-increasing proteins are eliminated in the preparation of monoparamunity inducers by the method described above for inactivating the attenuated myxomaviruses.

The monoparamunity inducer of the invention, also called PIND-MYXO, is based on the use of attenuated myxomaviruses or the paramunizing constituents thereof and is suitable on the basis of its paramunizing properties for the following prophylactic or therapeutic indications in a patient:

infectious factor diseases and mixed infections, chronic manifestations of infectious processes, refractory recurrent infections and chemotherapy-resistant bacterial and viral infections weakened defenses and dysregulations in the defense system of an organism threatened neonatal infection adjuvant therapy for certain neoplastic diseases, e.g. prevention of metastasis, reduction of side effects due to chemo- and radiotherapy regulation of homeostasis between the hormonal, circulatory, metabolic and nervous systems.

The paramunity inducers of the invention can be administered parenterally or locally to mammals, including humans, birds and reptiles. Local administration of paramunity inducers specifically stimulates the paraspecific defense mechanisms in the mucous membranes and in the skin. However, there is also a certain systemic effect. By contrast, parenterally applied paramunizations scarcely influence the local defense mechanisms in the skin and mucous membrane, preferably having a systemic effect.

Side effects do not occur even with numerous parenteral administrations carried out continuously in humans and animals. The indications for the use of PIND-MYXO are the same for animals and for humans. At the same time, in problem operations, specifically in the management of horses, pigs, dogs and cats, paramunization of neonates immediately on the day of birth and preferably on the first and possibly also the second day after birth is advisable. The single dose is about 0.5 to 5 ml of the dissolved lyophilisate, in horses and pigs the single dose is preferably 2 ml and in dogs and cats is preferably 0.5 ml on parenteral administration. It is advisable according to the invention to administer PIND-MYXO parenterally one day before and/or at the same time as specific protective inoculations in order to avoid secondary reactions and to assist the immunization on administration of vaccines.

One embodiment of the invention relates to the production of a pharmaceutical composition for local administration to induce paramunity in the skin and mucous membranes. The pharmaceutical composition preferably relates to a buccal or suckable tablet based on constituents of an attenuated and inactivated myxoma cell culture virus. The buccal tablets of the invention are preferably produced with addition of sorbitol, polyethylene glycol 6.00, potassium hydrogenphosphate, Tyrospirol tablet essence, Kollidon 25 and magnesium stearate. PIND-MYXO can, however, also be administered nasally, rectally or vaginally with suitable carriers.

The following examples are preferred embodiments of the invention and serve to explain the subject matter of the invention further.

EXAMPLE 1

The myxomavirus from the edematous subcutis of a European wild rabbit (genus *Oryctolagus*) suffering in a typical manner from myxomatosis was isolated as starting material for producing the monoparamunity inducer PIND-MYXO of the invention by culturing on the chorioallantoic membrane (CAM) of chicken eggs (Valo eggs) incubated for 10 days and was adapted three times by the method of Herrlich et al. in passages on the CAM (Herrlich A., Mayr A. and Munz E.: "Die Pocken", 2nd edition, Georg Thieme Verlag, Stuttgart, 1967). The third CAM passage was adapted in a 1st stage on Vero cells over 120 passages (ATCC CCL-81, WHO, American Type Culture Collection), replicated in a 2nd stage by 24 intermediate passages in AVIVER cell cultures, and cultured further in the 3rd phase in Vero cells. In total, about 300 passages aimed at attenuation were carried out. After these continuous end-dilution passages, the originally virulent myxomavirus was attenuated.

The attenuated myxomavirus is replicated in Vero cells. The Vero cell cultures are cultured using a completely synthetic medium consisting of MEM (minimal essential medium) plus 10% BMS (serum substitute medium) and 10% lactalbumin hydrolysate. The virus medium used after exchange with the culture medium is only MEM with 10% lactalbumin hydrolysate without BMS or without fetal calf serum and without antibiotics. All production methods are carried out at pH values above 7.25. Viral harvests with titers above $10^{6.5}$ $TCID_{50}$/ml serve as starting material for producing the monoparamunity inducer PIND-MYXO of the invention. Inactivation of the viral harvests with 0.05% beta-propiolactone and low-speed centrifugation are followed by addition of 5% of succinylated gelatin (polygeline) to the virus material before lyophilization.

The lyophilized product is stable at room temperatures and at temperatures of about 4° C. to −80° C. and can be kept without time restriction preferably at about 4° C. or else about −60° C. A volume of 1 ml of the lyophilisate dissolved in sterile distilled water corresponds to an inoculation dose. Deep intramuscular or local administration takes place (see examples 3, 4 and 5).

EXAMPLE 2

The PIND-MYXO inducer of the invention is administered in an analogous manner to the description in example 1 in dry form (lyophilisate not dissolved) locally onto the mucous membranes of the upper respiratory tract, preferably nasally, three times a day for prophylaxis or therapy (1 ml per application) of multifactorial infections (e.g. influenzal infections).

EXAMPLE 3

The PIND-MYXO inducer in liquid form produced as in example 1 is in an analogous manner rubbed in cutaneously to improve the perfusion of the skin, to speed up the healing of wounds and to treat varicose veins and chronic venous insufficiency (leg ulcer) in humans. The lyophilisate can for this purpose be taken up for example in greasy cream (e.g. Bepanthen, Linola fat), in which case the pH should be slightly alkaline. This preparation should be prepared fresh for each use. Administration is carried out several times a day by manual rubbing into the undamaged skin. Open wounds can be treated by dropwise application of the freshly dissolved product onto the wound regions. The treatment should take place each day until healed.

EXAMPLE 4

The monoparamunity inducer PIND-MYXO produced as in example 1 is analogously administered parenterally to prevent secondary reactions and to improve the result of inoculation one day before and simultaneously with a protective inoculation with conventional specific vaccines.

EXAMPLE 5

The monoparamunity inducer PIND-MYXO produced as in example 1 is processed analogously to buccal or suckable tablets. The production and use of the suckable tablets for local paramunization of the mucous membranes of the ear, nose, throat and mouth is novel and a constituent of the invention. Via the activated mucous membranes of the mouth there is not only a homing effect (migration of defense cells into mucous membranes of other organ systems), but also a partial parenteral paramunization. The following production method has proved suitable for the production of buccal and suckable tablets:

For the lyophilization, 5% Kollidon 25 (polyvinyl-pyrrolidone) is added instead of gelatin to the liquid inducer material. Urea, sorbitol, polyethylene glycol 6000 and magnesium stearate are required to produce the finished tablet. A recommended formula for a tablet with a weight of 500.5 mg in weight is:

| | |
|---|---|
| PIND-MYXO lyophilisate | 65 mg |
| Urea | 50 mg |
| Sorbitol | 267 mg |
| Polyethylene glycol 6000 | 118 mg |
| Magnesium stearate | 0.5 mg |
| Tablet weight | 500.5 mg |

The patient should take 4-6 tablets at regular intervals each day to achieve an optimal paramunization.

The following formula of a pharmaceutical composition has proved suitable for producing buccal tablets:

| | |
|---|---|
| PIND-MYXO lyophilisate | 155 mg |
| Sorbitol | 360 mg |
| Polyethylene glycol 6000 | 300 mg |

-continued

| | |
|---|---|
| Potassium dihydrogenphosphate (KH$_2$PO$_4$), anhydrous | 2 mg |
| Disodium hydrogenphosphate (Na$_2$HPO$_4$), anhydrous | 8 mg |
| Tyrospirol essence tablets | 0.8 mg |
| Magnesium stearate | 20 mg |
| Tablet weight | 805.8 mg |

The tablets slowly dissolve in the patient's mouth and can be swallowed after dissolving.

The clinical test results with the monoparamunity inducer of the invention, based on the lyophilisate of the myxomavirus strain M-2, which are compiled in tables 1 to 4 demonstrate the very good paramunizing activities of myxomavirus lyophilisates in humans. These data are equally applicable to other mammals as well as birds and reptiles.

TABLE 1

Clinical results with a monoparamunity inducer from attenuated myxoma cell culture virus in humans
- prophylactic uses -
(lyophilized inducer 1 OP (1 ml) intramuscular)

| Indications | Suitable administration methods |
|---|---|
| Periods of high infection pressure Stress Travel, examinations and similar stresses before or at the same time as protective inoculations | 2 injections before the stress at an interval of 24 hours |
| Chemotherapy, irradiation (reduction or prevention of secondary reactions) Operations (improvement in wound healing) | 1 injection each day or every 2nd day until the treatment is complete or until recovery |
| Maintenance of optimal defenses and hemodynamics Prophylaxis of cancer and hepatitides Improvement in wellbeing | 1-2 injections per month at an interval of 24 hours |

TABLE 2

Clinical results with a monoparamunity inducer from attenuated myxoma cell culture virus in humans
- therapeutic uses -
(lyophilized inducer 1 OP (1 ml) intramuscular)

| Indications | Suitable administration methods |
|---|---|
| Herpetic diseases (zoster, infectious mononucleosis, Herpes simplex, etc.) | 1 injection per day for 3-5 days or until the symptoms disappear; then one injection every 2nd or 3rd day until complete recovery |
| Chronic hepatitides | a "course" each month: 3 injections at intervals each of 24 hours |
| Influenzal infections viral and bacterial mixed infections (in combination with antibiotics or chemotherapy) | 1 administration per day until the symptoms disappear, then 1 injection every 2nd day until complete recovery |
| Immunodeficiencies and dysregulation of the defense systems (e.g. during or after chemotherapy) | 1. intensive treatment for 5-10 days: 1 injection per day 2. then 2 injections per week at an interval of 24 hours (treatment over a longer period possible) |
| Endotoxin damage | 1 injection a day for 7 days or until recovery |

TABLE 3

Effect of paramunization with myxoma inducer (PIND-MYXO) in patients with low immune parameters (7 days after PIND-MYXO administration)

| Patient | Patients' data Diagnosis/Therapy | Parameter (normal range) | Day 0 | Day 7 |
|---|---|---|---|---|
| A. S. female, 52 years | Immunosuppression | leukocytes (4000-10000/µl) | 4000 | 9400 |
| D. B. female, 54 years | Ulcerative colitis cortisone therapy | lymphocytes (900-3000/µl) | 620 | 1360 |
| | | CD4 cells (500-1800/µl) | 400 | 920 |
| | | CD8 cells (100-1000/µl) | 80 | 210 |
| U. S. male, 38 years | Immunological impairment | leukocytes (4000-10000/µl) | 3800 | 7400 |
| S. C. male, 43 years | Metastatic prostate carcinoma radiotherapy | leukocytes (4000-10000/µl) | 3800 | 9900 |
| B. M. female, 56 years | Susceptibility to infections | cytotoxic cells (30-360/µl) | 0 | 248 |

TABLE 4

Affect of paramunization with Myxoma inducer (PIND-MYXO) in patients with elevated immune parameters (7 days after PIND-MYXO administration)

| Patient | Diagnosis/ Therapy | Parameter (normal range) | Day 0 | Day 7 |
|---|---|---|---|---|
| G. P., female, 59 years | Cervical, breast carcinoma, susceptibility to infections | leukocytes (4000-10000/µl) | 12600 | 8600 |
| | | granulocytes (2400-6400/µl) | 8420 | 5930 |
| C. H. female, 51 years | Psychosomatic syndrome, obesity | leukocytes (4000-10000/µl) | 12700 | 6000 |
| | | granulocytes (2400-6400/µl) | 9270 | 4760 |

The invention claimed is:

1. A method for producing a paramunity inducer comprising:
   (a) isolating a myxomavirus from infected tissue of a rabbit;
   (b) adapting the virus to a permissive cell system;
   (c) passaging the adapted virus in Vero monkey kidney cells;
   (d) passaging the Vero cell passaged virus in a binary cell culture obtained by cell fusion between chicken embryo fibroblast cells and Vero monkey kidney cells;
   (e) passaging the binary cell passaged virus in Vero monkey kidney cells; and
   (f) selecting an attenuated myxomavirus that induces paramunity.

2. The method of claim 1, wherein the adaptation of the virus to a permissive cell system comprises culturing the virus on a chorioallantoic membrane of an incubated chicken egg.

3. The method of claim 1, wherein the virus is passaged at least 80 passages in Vero monkey kidney cells.

4. The method of claim 3, wherein the virus is passaged at least 120 passages in Vero monkey kidney cells.

5. The method of claim 4, wherein the virus is passaged at least 150 passages in Vero Monkey kidney cells.

6. The method of claim 1, wherein the virus is passaged at least 10 passages in the binary cell culture.

7. The method of claim 6, wherein the virus is passaged at least 25 passages in the binary cell culture.

8. The method of claim 7, wherein the virus is passaged 50 passages in the binary cell culture.

9. The method of claim 1, wherein the attenuated myxomavirus is inactivated with beta-propiolactone.

10. The method of claim 9, wherein the beta-propiolactone is at a concentration of 0.01%-1%.

11. A method for producing a paramunity inducer comprising:
   (a) isolating a myxomavirus from infected tissue of a rabbit;
   (b) adapting the virus to a permissive cell system;
   (c) passaging the adapted virus in Vero monkey kidney cells;
   (d) passaging the Vero cell passaged virus in a binary cell culture obtained by cell fusion between chicken embryo fibroblast cells and Vero monkey kidney cells;
   (e) passaging the binary cell passaged virus in Vero monkey kidney cells; and
   (f) selecting to generate an attenuated myxomavirus that induces paramunity and has lost the receptor properties of one or more myxomavirus interferon receptor, one or more myxomavirus tumor necrosis factor receptor, and one or more myxomavirus interleukin receptor.

12. The method of claim 11, wherein the attenuated myxomavirus has lost the receptor properties of the myxomavirus cytokine receptors IFNα-R, IFNγ-R, TNF-R, IL-1-R, IL-2-R, IL-6-R, and IL-12-R.

13. The method of claim 11, wherein the adaptation of the virus to a permissive cell system comprises culturing the virus on a chorioallantoic membrane of an incubated chicken egg.

14. The method of claim 11, wherein the virus is passaged at least 80 passages in Vero monkey kidney cells.

15. The method of claim 14, wherein the virus is passaged at least 120 passages in Vero monkey kidney cells.

16. The method of claim 15, wherein the virus is passaged at least 150 passages in Vero monkey kidney cells.

17. The method of claim 11, wherein the virus is passaged at least 10 passages in the binary cell culture.

18. The method of claim 17, wherein the virus is passaged at least 25 passages in the binary cell culture.

19. The method of claim 18, wherein the virus is passaged 50 passages in the binary cell culture.

20. The method of claim 11, wherein the attenuated myxomavirus is inactivated with beta-propiolactone.

21. The method of claim 20, wherein the beta-propiolactone is at a concentration of 0.01%-1%.

\* \* \* \* \*